United States Patent [19]

Bianchi

[11] Patent Number: 5,866,537
[45] Date of Patent: Feb. 2, 1999

[54] PHARMACEUTICAL AND/OR DIETETIC COMPOSITIONS WITH ANTIOXIDANT ACTIVITY CONTAINING CARNOSINE OR DERIVATIVES AND BRANCHED AMINO ACIDS

[75] Inventor: Roberto Bianchi, Milan, Italy

[73] Assignee: Farmila-Farmaceutici Milano S.R.L.

[21] Appl. No.: 952,437

[22] PCT Filed: May 15, 1996

[86] PCT No.: PCT/EP96/02079

§ 371 Date: Dec. 9, 1997

§ 102(e) Date: Dec. 9, 1997

[87] PCT Pub. No.: WO96/36348

PCT Pub. Date: Nov. 21, 1996

[30] Foreign Application Priority Data

May 19, 1995 [IT] Italy .................................. MI95A1021

[51] Int. Cl.$^6$ .......................... A61K 38/00; A61K 31/195
[52] U.S. Cl. .................................. 514/2; 514/561
[58] Field of Search ......................... 514/2, 561

[56] References Cited

FOREIGN PATENT DOCUMENTS 0 449 787 A2  10/1991  European Pat. Off. .

*Primary Examiner*—Raymond J. Henley, III
*Attorney, Agent, or Firm*—Bucknam And Archer

[57] ABSTRACT

A pharmaceutical or dietetic composition or both a pharmaceutical and dietetic composition having antioxidant activity contains carnosine or derivatives of carnosine and leucine, isoleucine and valine. It may also contain other components such as carnitine, vitamins, oligoelements and bioflavanoids.

3 Claims, No Drawings

PHARMACEUTICAL AND/OR DIETETIC COMPOSITIONS WITH ANTIOXIDANT ACTIVITY CONTAINING CARNOSINE OR DERIVATIVES AND BRANCHED AMINO ACIDS

FIELD OF THE INVENTION

This application is a 371 of PCT/EP96/02079 filed May 15, 1996.

The present invention relates to pharmaceutical and/or dietetic compositions with antioxidant activity, consisting of
a) carnosine and derivatives thereof, as better specified below, and of
b) leucine and/or isoleucine and/or valine; and optionally also of
c) carnitine, derivatives thereof (as better specified below) and creatine; and/or
d) oligoelements; and/or
e) vitamins; and/or
f) bioflavonoids.

BACKGROUND OF THE PRIOR ART

Free radicals and the peroxidative processes caused by them have been known for a long time to be one of the causes of the structural and functional degradations of human tissues during aging and of a number of pathologies related to them: tumours; diabetes; hypertension; muscular excessive strain; radiation and sunburn damages; intoxications; ischemia; atherosclerosis; hyperthermia; cerebral traumas; inflammations; cataract; multiple sclerosis; Down syndrome, Parkinson's disease, Alzheimer's disease; dermatitis; muscular dystrophy; obesity; hyperlipidemia; hypercholesterolemia; tabagism; alcoholism, etc. (B. Cestaro, (1994), in "Per una vita inossidabile", ETASLIBRI—RCS Medicine, pp. 7–59; G. D. Bompiani, A. Galluzzo, (1990), in "Radicali Liberi in Fisiologia and Minerva Medica", pp. 3–280; Supplement to "The American Journal of Clinical Nutrition" vol. 53 (n. 1), 1991. pp. 189S–391S; "Radicali Liberi in Medicina", Periodici UTET Scientifici n. 1. dicembre 1993. pp. 1–57; "Lipid Peroxidation: part II Pathological Implications", (1987), Chem and Physics of Lipids, vol. 45 (n. 2–4), pp. 103–353).

Therefore it is important, in order to prevent the aging processes and related pathologies, to keep the concentration of the natural antioxidant molecules, ("free radical scavengers") which are the physiological defenses against free radicals, high both in the different tissues of the organism and in the blood stream, with which a continuous functional interchange occurs; in other words, blood (and the erythrocytes contained therein) can act as a carrier: 1) to provide the necessary antioxydants (both exogenous and deriving from, for example, the oral administration, and taken from endogenous deposits) to a certain tissue (which is at that time subjected to a specific pathological stress condition); 2) to drain the products from the peroxidative processes accumulated in a specific district of the organism.

It is therefore evident that an appropriate chemical-clinical evaluation of the sensitivity of plasma and/or of the erythrocytes (i.e. of the different tissues of the organism) to peroxidation can be an effective prognostic means to evaluate the efficiency of human antioxidant defenses and the capability of the body of defending against the damage induced by said dysmetabolic processes, typical of aging and of the above cited pathologies.

Carnosine (β-alanyl-L-histidine) and some derivatives thereof (homocarnosine, acetylcarnosine, acetylhomocarnosine, etc.) have been known for some time to be among the most important natural antioxidant agents (Boldyrev A., Severin S., (1990), Adv. Enz. Reg., 30. 175–194; Kohen R. et al., (1988), Proc. Natl. Acad. Sci. USA, 85. 3175–79; Yoshikawa T. et al., (1991), Biochim. Biophys. Acta, 1115. 15–22) and the administration of these compounds would allow to cause an effective therapeutical activity in a number of the above mentioned pathologies (Davey C. L., (1960), Arch. Biochem. Biophys., 89. 303–308; Severin S., (1964); Proc. 6th Intern. Biochem. Congress, 45–61; Nagai K. and Suda T., (1988), Meth. Find. Exp. Clin. Pharmacol., 10. 497–507; Boldyrev A., (1990), Int. J. Biochem., 22. 129–132; Kurelle E. et al., (1991), Byul. Exp. Biol. Med., 112. 52–53; Boldyrev A. et al.; (1993), Int. J. Biochem., 25 1101–1107; Boldyrev A. et al., (1993), Mol. Chem. Neuropathol., 19. 185–192), particularly where the peroxidative damage induced by free radicals is one of the main causes in inducing and/or worsening the pathology. The antiradicalic activity of exogenous carnosine (or of the homologues thereof) is however restricted by the instability shown by said peptide towards the enzyme carnosinase, which is capable of hydrolyzing it into aminoacids components. The carnosinase is present both in the bloodstream and in the various tissue districts.

It has now been surprisingly found that the combination of carnosine with the branched amino acids leucine, isoleucine and valine induces an effect synergistic with the carnosine antioxidant activity, prolonging it in time, at equal doses. Since a direct antiradicalic effect of said amino acids (even if they are known to promote a therapeutical activity in different tissues, particularly in the skeletal muscle, thanks to their capability of increasing the cell energetic metabolism (R. Bernardi, in "Aminoacidi ed Esercizio", (1992), EDI-ERMES editore, Milan, Italy)), it is believed (without however limiting the scope of the invention) that such a synergistic effect can be ascribed to an inhibitory action on carnosinase, which prolongs the half-life of the circulating dipeptide and increases the bioavailability due to both the reaching of the specific tissue targets and the antioxidant action.

As an alternative, non-limiting interpretation, the increased antiradicalic effectiveness could be related to: 1) the cell energetic metabolic increase by the branched amino acids, which would lead to a reduction in the formation of free radicals, particularly those of the oxygen; 2) the indirect antioxidant action mediated by the cell activation induced by said amino acids, via unknown mechanisms and mediators.

SUMMARY OF THE INVENTION

The invention provides compositions for pharmaceutical and/or dietetic use, which lead—after in vivo administration by suitable galenical formulations—to an unforeseen synergistic increase in the antioxidant activity of carnosine (and/or of the derivatives thereof).

Said compositions are characterized in that they contain as basic, necessary components, in the suitable ratios:
a) carnosine and/or derivatives thereof, such as homocarnosine, anserine, ofidine and/or the pharmacologically compatible inorganic and organic salts and/or the acyl derivatives thereof with pharmacologically compatible organic acids, and the inorganic salts thereof;
b) one or more branched amino acids, in suitable ratios, such as: leucine, isoleucine and valine, both in the free form and in the salified one with inorganic or organic bases or acids, provided that they are pharmacologically compatible, and/or the acyl derivatives thereof, salified with inorganic or organic bases, and/or the esters thereof with straight or branched alcohols, optionally salified with inorganic or organic acids.

Moreover, supplementary components of the compositions, depending on the intended final therapeutical characteristics, are:

c) carnitine and/or water-soluble acyl derivatives thereof (for example acetylcarnitine, propionyl-carnitine, etc.), which are known to have antioxidant activity as well as therapeutic activity in a number of the above mentioned pathologies, in particular in those of nervous system (Geremia E. et al., (1988), Med. Sci. Res., vol. 16 (n. 13), 699–700; Calabrese V. et al., in "Brain Metabolism and Aging", Meeting in Florence (19/1/1989) pp. 42–44; Ghirardi O. et al., in "VII General Meeting of Eur. Soc. for Neurochem." Leipzig (23/7/1990); Tesco-Latorraca S. et al., (1992), Dementia, vol. 3 (n. 1) pp. 58–60), and creatinine;

d) oligoelements such as: iron, zinc, manganese, magnesium, copper, cobalt, chrome, molybdenum, vanadium and selenium, in the form of suitable salts of inorganic or organic acids or complexes with pharmacologically compatible amino acids, polypeptides or proteins;

moreover, the following constituents can also be part of the compositions for the alimentary use:

e) vitamins (A, B15, C, D3, E)

f) bioflavonoids (such as those deriving from the citruses: orange, lemon, grapefruit).

The galenical formulations suitable for the oral administration are also part of the invention, provided that they are based on said compositions: swallowable tablets, divisible or not; suitably flavored chewable tablets; hard- and soft-gelatin capsules; granulates for the extemporary preparation of aqueous solutions, suitably flavored and added with pharmacologically inert excipients such as various sugars (sachets, solids for use in plunger caps, etc.); suitably flavored chewing gums; wafer sheets; ready-to-use aqueous solutions, optionally flavoured and added with suitable stabilizers, etc.

The preparation of said galenical formulations can require the simple dry mixing of the components or the previous dry- or humid- granulation, which techniques are known to those skilled in the art.

Said formulations are used successfully in the prevention and in the treatment of organic aging and/or of the pathologies related thereto and characterized by an increase in the degenerative peroxidation processes induced by free radicals.

DETAILED DISCLOSURE OF THE INVENTION

The characteristics and the advantages of the compositions according to the present invention will be further illustrated in the following disclosure.

Said compositions contain as basic active components:

a) carnosine (β-alanyl-L-histidine) and/or homocarnosine (τ-butyryl-L-histidine) and/or anserine (N1-methyl-β-alanyl-L-histidine) and/or ofidine (N3-methyl-β-alanyl-L-histidine), and/or the pharmacologically compatible inorganic or organic salts thereof and/or the acyl derivatives thereof with pharmacologically compatible acids organic, and the inorganic salts thereof;

the content in the constituents a) in the final mixture ranging from 1% to 50% by weight (with the exception of the inert material used for the galenical formulation, also including any sugars added and flavours), preferably from 15% to 25%; and b) one or more branched amino acids, in suitable ratios, such as: leucine, isoleucine and valine, both in the free form and in the salified one with inorganic or organic bases or acids, provided that they are pharmacologically compatible, and/or the acyl derivatives thereof, salified with inorganic or organic bases, and/or the esters thereof with straight or branched alcohols, optionally salified with inorganic or organic acids;

the weight ratio of the three amino acids ranging, in the order, from 1:1:1 to 1:0:0, compositions in which leucine is at least 20% of the mixture of the three amino acids being preferred; the content in the constituents b) in the final mixture ranging from 5% to 80% by weight (with the exception of the inert materials used for the galenical formulation, also including any sugars added and flavors), ranging preferably from 50% to 70%.

The compositions according to the invention can moreover contain one or more of the following accessory components:

c) carnitine (3-carboxy-2-hydroxy-N,N,N-trimethyl-1-propanamine inner salt) and/or water-soluble acyl derivatives thereof (for example: acetylcarnitine, propionylcarnitine, etc.), and creatine;

the content in c) in the final mixture ranging from 0% to 20% by weight (with the exception of the inert materials used for the galenical formulation, also including any sugars added and flavors), preferably from 2.5% to 5%;

d) oligoelements such as: iron, zinc, manganese, magnesium, copper, cobalt, chrome, molybdenum, vanadium and selenium in the form of salts (fumarate, sulfate, oxide, etc.) or complexes with pharmacologically compatible amino acids, polipeptides or proteins;

the amount of c) ranging from 0 mg to 30 mg, depending on the element in the final galenical formulation, for single administration;

e) vitamins (A, B15. C, D3. E) in the usual amounts made use of in the formulations for the alimentary use;

f) bioflavonoids (such as those deriving from citruses: orange, lemon, grapefruit) in the usual amounts made use of in the formulations for the alimentary use.

The preparation of the formulations of the present invention in forms for the oral administration, as reported above, needs no specific techniques, since the different powders have a good mixibility and/or are easily water-soluble also in admixture.

The compositions of the invention are prepared in the usual oral pharmaceutical forms: swallable tablets, divisible or not; suitably flavored chewable tablets; hard- and soft-gelatin capsules; granulates for the extemporary preparation of aqueous solutions, suitably flavored and added with pharmacologically inert excipients such as various sugars (sachets, solids for use in plunger caps, etc.); suitably flavored chewing gums; wafer sheets; ready-to-use aqueous solutions, optionally flavored and added with suitable stabilizers, etc.

By way of non-limiting example, some formulations according to the invention are reported below.

In the following examples, the compositions are expressed as active ingredient content in grams, independently of the salification, referred to 100 g of final mixture; the components used can be in the form of the free bases or salts, the type of anion being shown in brackets.

EXAMPLE 1

Example of a Formulation of the Invention

The composition can be prepared in the form of capsules or soluble, effervescent tablets, sachets etc., as described above, after preparing a humid granulate in which the branched amino acids are dissolved in water and said solution is subsequently sprayed on the homogeneous solid mixture obtained by dry mixing (for example in suitable coating pans) of the other suitably powdered components (for example: in a ball mill). The final mixture is then dried in dry air stream at a temperature below 45° C.

In the case di soluble effervescent formulations, to the final product, in suitable controlled-humidity environment, is added dry tartaric or citric acids, mixed to homogeneity and then the procedure is repeated with sodium bicarbonate. After that, the product is granulated with the usual techniques. The compression of said final mixture gives the effervescent tablets or sachets, whereas, by direct partition of the granulate, before the addition of the effervescent components, the capsules or the tablets are prepared.

Carnosine (base or hydrochloride):15
Leucine (base, hydrochloride, sulfate, acetate etc.):15
Isoleucine (base, hydrochloride, sulfate, acetate etc.):15
Valine (base, hydrochloride, sulfate, acetate etc.):15
Carnitine (base, hydrochloride etc.):15
Arginine (base, hydrochloride, glutamate etc.):15
Mg (carbonate-hydroxide, basic citrate, lactate, sulfate):8.5
Zinc (carbonate, lactate, sulfate etc.):0.5
Copper (acetate, basic carbonate, gluconate, sulfate etc.):0.25
Iron (gluconate, albuminate, fumarate, proteinate etc.):0.75.

EXAMPLE 2

Carnosine (base or hydrochloride):35
Leucine (base, hydrochloride, sulfate, acetate etc.):50
Arginine (base, hydrochloride, glutamate etc.):10
Mg (carbonate-hydroxide, basic citrate, lactate, sulfate):3.5
Zinc (carbonate, lactate, sulfate etc.):0.5
Copper (acetate, basic carbonate, gluconate, sulfate etc.):0.25
Iron (gluconate, albuminate, fumarate, proteinate etc.):0.75.

EXAMPLE 3

Carnosine (base or hydrochloride):18
Leucine (base, hydrochloride, sulfate, acetate etc.):16
Isoleucine (base, hydrochloride, sulfate, acetate etc.):16
Valine (base, hydrochloride, sulfate, acetate etc.):16
Carnitine (base, hydrochloride etc.):7.5
Creatine (base):7.5
Arginine (base, hydrochloride, glutamate etc.):15
Mg (carbonate-hydroxide, basic citrate, lactate, sulfate):2.5
Zinc (carbonate, lactate, sulfate etc.):0.5
Copper (acetate, basic carbonate, gluconate, sulfate etc.):0.25
Iron (gluconate, albuminate, fumarate, proteinate etc.):0.75.

EXAMPLE 4

Carnosine (base or hydrochloride):25
Leucine (base, hydrochloride, sulfate, acetate etc.):25
Isoleucine (base, hydrochloride, sulfate, acetate etc.):10
Valine:6
Creatine (base):20
Arginine (base, hydrochloride, glutamate etc.):10
Mg (carbonate-hydroxide, basic citrate, lactate, sulfate):2.5
Zinc (carbonate, lactate, sulfate etc.):0.5
Copper (acetate, basic carbonate, gluconate, sulfate etc.):0.25
Iron (gluconate, albuminate, fumarate, proteinate etc.):0.75.

EXAMPLE 5

Carnosine (base or hydrochloride):20
Leucine (base, hydrochloride, sulfate, acetate etc.):25
Isoleucine (base, hydrochloride, sulfate, acetate etc.):15
Creatine (base):20
Arginine (base, hydrochloride, glutamate etc.):15
Mg (carbonate-hydroxide, basic citrate, lactate, sulfate):2.5
Zinc (carbonate, lactate, sulfate etc.):0.5
Copper (acetate, basic carbonate, gluconate, sulfate etc.):0.15
Iron (gluconate, albuminate, fumarate, proteinate etc.):0.75
Manganese (sulfate, gluconate):0.10
Vitamins B15/C/E/D3:150 mg
Lemon and orange bioflavanoids: 200 mg.

Pharmacological and/or Dietetic Tests

In order to study the pharmacological and/or dietetic characteristics of the compositions according to the present invention, tests were carried out to evaluate the following effects in rats subjected to an ipovitaminic, hyperlipidemizing and hypercholesterolemizing diet (which is known to be capable of promoting the tissue and plasma peroxidation processes):

1°) effect of the compositions on the lipoperoxides gastric content (measured as malonildialdehye nmoles/ml)
2°) effect of the compositions on the lipoperoxides hepatic content (measured as malonyldialdehyde nmoles/g)
3°) effect of the compositions on the lipoperoxides cerebral content (measured as malonyldialdehyde nmoles/g)
4°) effect of the compositions on the lipoperoxides content in the heart (measured as malonyldialdehyde nmoles/g).
36 Male rats weighing 180–200 g were used.

The animals were subjected for 20 days to a standard hyperlipidemizing and hypercolesterolemizing diet consisting of: 20% caseine, a 3.5% mixture of oligoelements and mineral salts, a 0.1% mixture of vitamins, 0.2% choline bitartrate, 2% cellulose powder, 0.5% chloesterol, 0.25. sodium cholate, 62.44% saccharose and 10.9% lard. During that time, the animals were divided into in 6 groups which received as an "ad libitum" available drink:

1° group: control (only water)
2° group: Test A (a 0.75% CARNOSINE aqueous solution)
3° group: Test B (a 0.25% CARNITINE aqueous solution)
4° group: Test C (an aqueous solution of 4% branched amino acids; leucine/isoleucine/valine=30/0.5/0.5)
5° group: Test D (a 0.75% CARNOSINE and 4% branched amino acids aqueous solution as in Test C)
6° group: Test E (a 0.75% CARNOSINE aqueous solution plus 0.25% CARNITINE with 4% branched amino acids as in the above Test C).

At end of the test the animals were killed to take both blood samples and the various organs (liver, brain, and heart) on which the lipoperoxides content was evaluated dosing malonyldialdehyde, according to the procedure by Yagi (YAGI K, (1982), in "Lipid peroxides in biology and medicine", Academic Press, New York, pp. 324–40). The results of the lipoperoxides content in plasma are reported in Table I.

TABLE I

Changes in lipoperoxides content in the plasma (expressed as malonyldialdehyde nmoles/ml) as the function of the different compositions administered.

|  | malonyldialdehyde nmoles/ml | percent variation compared with the control |
|---|---|---|
| Control | 4.2 ± 0.7 | — |
| Test A (Carnosine) | 3.6 ± 0.6 | −14.2% |
| Test B (Carnitine) | 4.2 ± 0.8 | — |
| Test C (Branched A.A.) | 4.3 ± 0.5 | +2.3% |
| Test D (Carnosine + Branched A.A.) | 3.0 ± 0.7 | −28.5% |
| Test E (Carnosine + Carnitine + Branched A.A.) | 2.7 ± 0.4 | −35.7% |

It is evident that carnosine administration significantly reduces lipoperoxides plasma contents (−14.2%), whereas no effects result from the administration of carnitine alone and an even negative effect to the therapeutical purposes (+2.3%) is observed after administration of the only branched A.A.. A surprisingly favourable, synergistic therapeutical effect, on the other hand, results from the simultaneous administration of carnosine+branched A.A. (−28.5%) and of carnosine+branched A.A.+carnitine (−35.7%).

The results referred to the lipoperoxides content in the liver are reported in Table II.

TABLE II

Changes in the lipoperoxides content in the liver (expressed as malonyldialdehyde nmoles/g. of fresh tissue) as a function of the different compositions administered.

|  | malonyldialdehyde nmoles/g. of fresh tissue | percent variation compared with the control |
|---|---|---|
| Control | 42 ± 7 | — |
| Test A (Carnosine) | 39 ± 8 | −9.5% |
| Test B (Carnitine) | 43 ± 6 | +2.3% |
| Test C (Branched A.A.) | 44 ± 7 | +4.7% |
| Test D (Carnosine + Branched A.A.) | 32 ± 6 | −23.8% |
| Test E (Carnosine + Carnitine + Branched A.A.) | 30 ± 5 | −28.5% |

It is evident that the carnosine administration significantly reduces the hepatic lipoperoxides content (−9.5%). On the contrary, a mildly negative therapeutic effect results from the administration of the only carnitine (+2.3%) and of the only branched A.A. (+4.7%). On the other hand, a surprisingly favourable, synergistic therapeutical effect is obtained by the simultaneous administration of carnosine+branched A.A. (−23.8%) and of carnosine+branched A.A.+carnitine (−28.5%).

The results referred to the lipoperoxides content in brain are reported in Table III.

TABLE III

Changes of the lipoperoxides content in brain (expressed as malonyldialdehyde nmoles/g. of fresh tissue) as a function of the different compositions administered.

|  | malonyldialdehyde nmoles/g. of fresh tissue | percent variation compared with the control |
|---|---|---|
| Control | 102 ± 6 | — |
| Test A (Carnosine) | 89 ± 7 | −12.7% |
| Test B (Carnitine) | 106 ± 5 | +3.9% |
| Test C (Branched A.A.) | 102 ± 8 | — |
| Test D (Carnosine + Branched A.A.) | 69 ± 7 | −33.3% |
| Test E (Carnosine + Carnitine + Branched A.A.) | 68 ± 4 | −32.3% |

From this Table it is evinced that carnosine administration significantly reduces the brain lipoperoxides content (−12.7%), whereas no therapeutically favorable results are observed after the administration of the only carnitine (+3.9%) or of the only branched A.A. (no changes compared with the controls).

On the contrary, a surprisingly favorable therapeutical, synergistic effect results from the simultaneous administration of carnosine+branched A.A. (−32.3%) and of carnosine+carnitine+branched A.A. (33.3%). The results referred to the lipoperoxides content in the heart are reported, finally, in Table IV.

TABLE IV

Changes of lipoperoxides content in the heart (expressed as malonyldialdehyde nmoles/g. of fresh tissue) as a function of the different compositions administered.

|  | malonyldialdehyde nmoles/g. of fresh tissue | percent variation compared with the control |
|---|---|---|
| Control | 45 ± 6 | — |
| Test A (Carnosine) | 36 ± 7 | −20.0% |
| Test B (Carnitine) | 45 ± 4 | — |
| Test C (Branched A.A.) | 46 ± 5 | +2.2% |
| Test D (Carnosine + Branched A.A.) | 29 ± 4 | −35.5% |
| Test E (Carnosine + Carnitine + Branched A.A.) | 28 ± 5 | −37.7% |

As it can be observed, the carnosine administration significantly reduces the content in brain lipoperoxides (−20%). On the contrary, the administration of only carnitine (no changes compared with the controls) or of the only branched A.A. (+2.2%) cause no or even adverse effects for the therapeutical purposes of preventing the peroxidative damage. A surprisingly favorable, synergistic therapeutical effect is obtained, on the other hand, after the simultaneous administration of carnosine+branched A.A. (−35.5%) and of carnosine+carnitine+branched A.A. (−37.7%).

The results from the tests above described show that the compositions of the invention can be used to increase the levels of antioxidants defenses and to prevent an increase in the peroxidative processes (in blood and in the different tissues of human body) occurring during aging and in a number of pathologies (see the references above) which are often related to aging. Therefore, said compositions can be used for the preparation of pharmaceutical and/or dietetic forms for the oral administration oral alone [a)+b)+c) or a)+b)] or in combination with other substances such as emulsifiers, other antioxidants, heavy metal chelating agents and pharmacologically (and/or dietotherapeutically) acceptable conventional excipients.

The daily dosage of the compositions [a)+b)+c) or a)+b)] will vary depending on the use which can be both dietotherapeutically prophylactic or therapeutical in the different pathologies, but it will generally range, for prophylactic purposes (dietetic use) from 0.1 to 10 mg/kg/die of carnosine (and derivatives), from 0 to 2.5 mg/kg/die of carnitine (and derivatives) and from 0.1 to 100 mg/kg/die for the branched A.A. (and derivatives) and for the therapeutical purposes (therapeutic use) from 1 to 100 mg/kg/die of carnosine (and derivatives), from 0 to 25 mg/kg/die of carnitine (and derivatives) and from 1 to 500 mg/kg/die for the branched A.A. and derivatives.

We claim:

1. A pharmaceutical or dietetic composition or both a pharmaceutical and dietetic composition containing:
    a) a member selected from the group consisting of carnosine, homocarnosine, anserine, ofidine, pharmacologically compatible inorganic and organic salts thereof, acyl derivatives thereof with pharmacologically compatible organic acids and inorganic salts thereof, said constituent a) being present in the amount of 15–25% by weight,
    b) leucine, isoleucine and valine, both in the free form and in the salified one with inorganic or organic pharmacologically compatible bases or acids, acyl derivatives thereof salified with inorganic or organic bases, and esters thereof with straight or branched alcohols, salified with inorganic or organic acids, wherein leucine is at least 20% of the mixture of the three amino acids, the content of the said constituents b) ranges from 50 to 70% by weight,
and an additive which is a member selected from the group consisting of carnitine, derivatives thereof and creatine; oligoelements; vitamins, bioflavanoids and mixtures thereof.

2. A pharmaceutical or dietetic composition or both a pharmaceutical and dietetic composition which comprises
    a) carnosine,
    b) leucine, isoleucine and valine, the total amount of of leucine, isoleucine and valine being 5.3 times the amount of carnosine,
and an additive which is a member selected from the group consisting of carnitine, derivatives thereof and creatine; oligoelements; vitamins, bioflavanoids and mixtures thereof.

3. This composition according to claim 2, which is an aqueous solution and wherein said additive is carnitine.

* * * * *